(12) United States Patent
Iwasaki et al.

(10) Patent No.: US 11,577,190 B2
(45) Date of Patent: Feb. 14, 2023

(54) RECOVERED-CARBON-DIOXIDE PURIFYING METHOD AND METHIONINE MANUFACTURING METHOD INCLUDING RECOVERED-CARBON-DIOXIDE PURIFYING STEP

(71) Applicant: SUMITOMO CHEMICAL COMPANY, LIMITED, Tokyo (JP)

(72) Inventors: Ryosuke Iwasaki, Niihama (JP); Takuya Katayama, Niihama (JP); Norihito Omoto, Niihama (JP); Yoshiyuki Koizumi, Niihama (JP); Ryousuke Katagami, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 691 days.

(21) Appl. No.: 16/608,066

(22) PCT Filed: Apr. 27, 2018

(86) PCT No.: PCT/JP2018/017205
§ 371 (c)(1),
(2) Date: Dec. 6, 2019

(87) PCT Pub. No.: WO2018/199292
PCT Pub. Date: Nov. 1, 2018

(65) Prior Publication Data
US 2020/0188834 A1 Jun. 18, 2020

(30) Foreign Application Priority Data

Apr. 27, 2017 (JP) .............................. JP2017-087749

(51) Int. Cl.
| | | |
|---|---|---|
| *B01D 53/02* | (2006.01) | |
| *B01D 53/96* | (2006.01) | |
| *B01J 20/20* | (2006.01) | |
| *B01J 20/28* | (2006.01) | |
| *C07C 319/20* | (2006.01) | |
| *C07C 319/28* | (2006.01) | |
| *B01D 9/00* | (2006.01) | |
| *C07C 323/57* | (2006.01) | |

(52) U.S. Cl.
CPC ............. *B01D 53/02* (2013.01); *B01D 53/96* (2013.01); *B01J 20/20* (2013.01); *B01J 20/28066* (2013.01); *B01J 20/28071* (2013.01); *B01J 20/28073* (2013.01); *C07C 319/20* (2013.01); *C07C 319/28* (2013.01); *B01D 9/005* (2013.01); *C07C 323/57* (2013.01)

(58) Field of Classification Search
CPC ........ B01D 9/005; B01D 53/02; B01D 53/04; B01D 53/96; B01D 2253/102; B01D 2257/702; B01J 20/20; B01J 20/28; B01J 20/28066; B01J 20/28071; B01J 20/28073; C07C 319/20; C07C 319/28; C07C 323/57; C07B 61/00; C01B 32/30; C01B 32/50; C01P 2004/60; C01P 2006/12; C01P 2006/14; Y02P 20/151
USPC ............. 562/559; 95/139, 92, 159, 149, 235
See application file for complete search history.

(56) References Cited

U.S. PATENT DOCUMENTS

| | | | |
|---|---|---|---|
| 3,636,008 A | 1/1972 | Shima et al. | |
| 5,770,769 A | 6/1998 | Geiger et al. | |
| 7,655,072 B2 | 2/2010 | Hasselbach et al. | |
| 10,961,186 B2* | 3/2021 | Yamashita | ............ C07C 319/28 |
| 2006/0016334 A1 | 1/2006 | Hasselbach et al. | |
| 2010/0004486 A1 | 1/2010 | Koizumi et al. | |
| 2010/0206165 A1 | 8/2010 | Alban et al. | |

FOREIGN PATENT DOCUMENTS

| | | |
|---|---|---|
| CN | 1376671 A | 10/2002 |
| CN | 101602700 A | 12/2009 |
| CN | 101842143 A | 9/2010 |
| EP | 1 256 571 A1 | 11/2002 |
| EP | 1 768 764 B1 | 8/2012 |
| JP | 4-124171 A | 4/1992 |
| JP | 2003-104958 A | 4/2003 |
| JP | 2004-81192 A | 3/2004 |
| JP | 2008-506520 A | 3/2008 |
| JP | 4881299 B2 | 2/2012 |

OTHER PUBLICATIONS

Japanese Notice of Reasons for Refusal for Japanese Application No. 2019-514656, dated May 10, 2022, with an English translation.
International Preliminary Report on Patentability and the Written Opinion of the International Searching Authority for International Application No. PCT/JP2018/017205, dated Oct. 29, 2019.
International Search Report for International Application No. PCT/JP2018/017205, dated Jul. 10, 2018.
Xue et al., "Mainstream Smoke Gas Phase Filtration Performance of Adsorption Materials Evaluated With a Puff-by-Puff Multiplex GC-MS Method", Contributions to Tobacco Research, vol. 20, No. 4, Dec. 2002, pp. 251-256.
Chinese Office Action and Search Report (including an English translation thereof) issued in the corresponding Chinese Patent Application No. 201880027556.6 dated Jun. 6, 2022.
Abstract of Kozlov et al., "Use of activated carbons for the removal of acrolein from waste gases," Lakokrasochnye Materialy i Ikh Primenenie, 1979.

(Continued)

*Primary Examiner* — Elizabeth D Wood
(74) *Attorney, Agent, or Firm* — Birch, Stewart, Kolasch & Birch, LLP

(57) ABSTRACT

The present invention provides a method for purifying carbon dioxide gas characterized in that carbon dioxide gas containing at least one of 3-methylmercaptopropionaldehyde and acrolein is contacted with activated carbon to remove at least one of the 3-methylmercaptopropionaldehyde and acrolein. The present invention provides also a method for producing methionine comprising the purification step of the recovered carbon dioxide.

3 Claims, 3 Drawing Sheets

(56) References Cited

OTHER PUBLICATIONS

European Patent Office Communication and extended search report issued in the European Patent Application No. 18790049.3 dated Nov. 24, 2020.
Singaporean Written Opinion issued in the Singaporean Patent Application No. 11201911242Q dated Oct. 2, 2020.

* cited by examiner

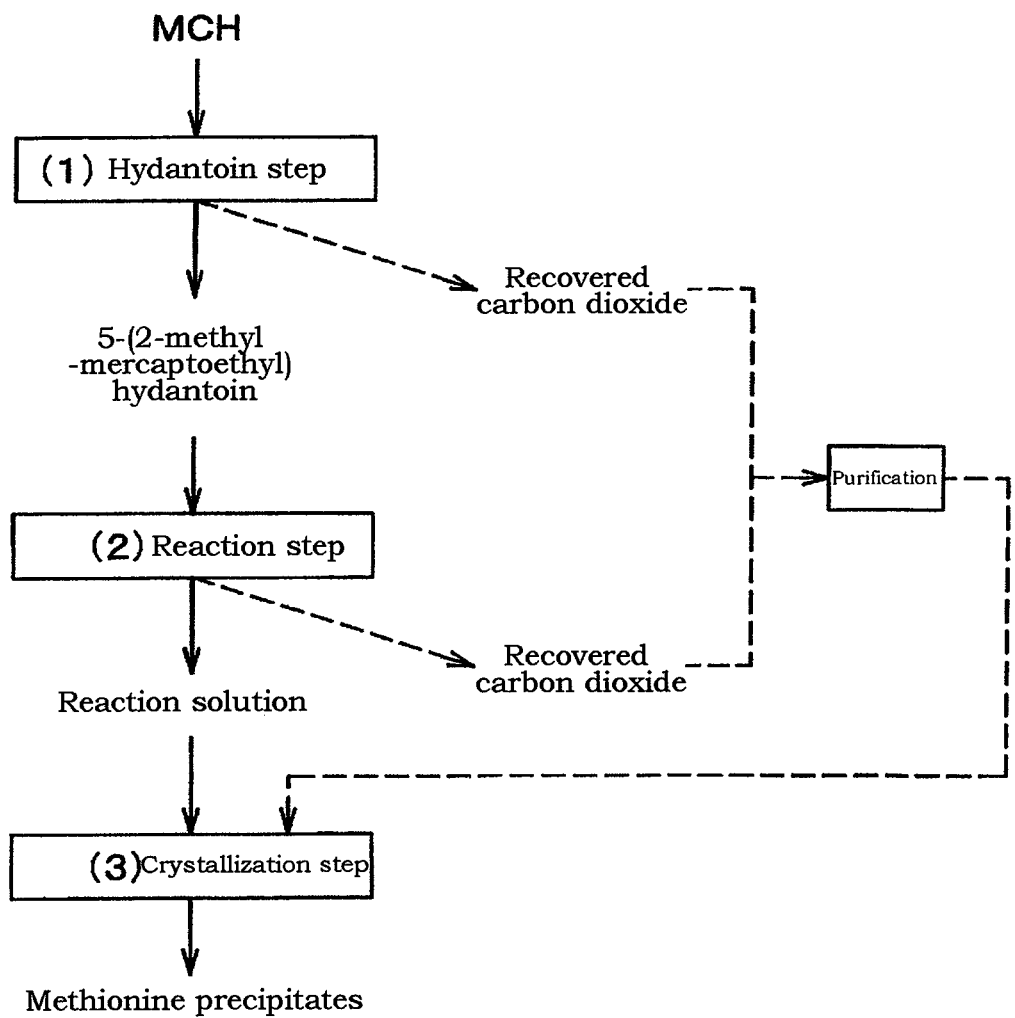
[Fig. 1]

[Fig. 2]
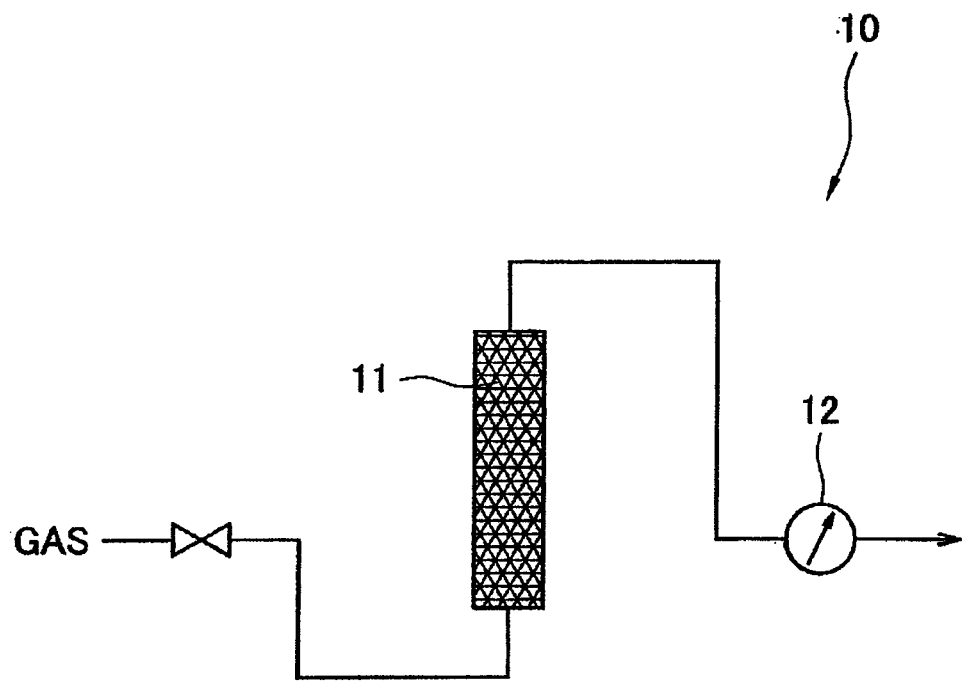

[Fig. 3]
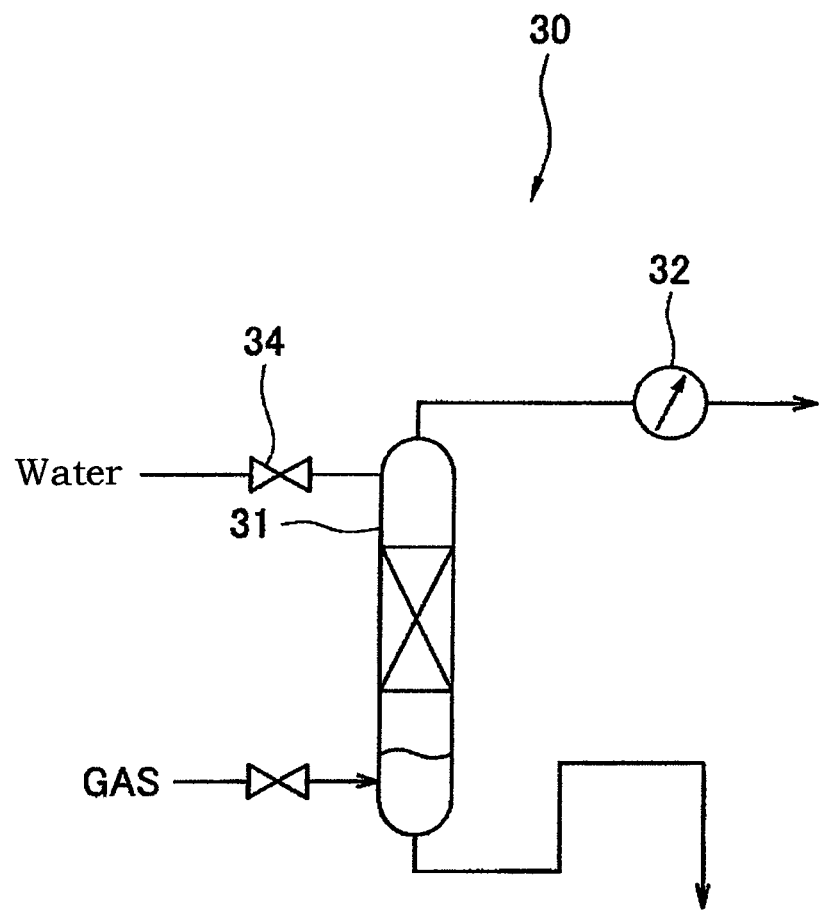

RECOVERED-CARBON-DIOXIDE PURIFYING METHOD AND METHIONINE MANUFACTURING METHOD INCLUDING RECOVERED-CARBON-DIOXIDE PURIFYING STEP

TECHNICAL FIELD

This application claims priority to and the benefit of Japanese Patent Application No. 2017-087749 filed Apr. 27, 2017, the entire contents of which are incorporated herein by reference.

The present invention relates to a method for purifying recovered carbon dioxide, and a method for preparing methionine comprising a step of purifying recovered carbon dioxide. In detail, the present invention relates to a purifying method for purifying recovered carbon dioxide with activated carbon, a method for preparing methionine comprising the same step. As used herein, "recovered carbon dioxide" means a gas containing at least one of 3-methylmercaptopropionaldehyde (hereinafter, sometimes referred to as "M-aldehyde") and acrolein (hereinafter, sometimes referred to as "ACR") and pure carbon dioxide.

BACKGROUND ART

Methionine is an essential amino acid that cannot be synthesized in an animal body, and is widely used as a feed additive for animal, and also is industrially produced by a chemical plant. In such a chemical plant, if it is intended to expand the production scale of methionine, an improvement is required from the viewpoint of cost reduction and environmental burden reduction.

Patent Document 1 discloses that a hydantoin reactor for forming 5-(2-methylmercaptoethyl) hydantoin is used in the production of methionine. From this hydantoin reactor, an exhaust gas containing carbon dioxide flows out. It is disclosed in Patent Document 1 that the exhaust gas is purified with water, thereby methyl mercaptan (hereinafter, sometimes referred to as "MM") contained in the exhaust gas is removed, and the purified exhaust gas is used in a process for precipitating methionine.

CITATION LIST

Patent Document

Patent Document 1: JP 4881299 B

SUMMARY OF THE INVENTION

Problems to be Solved by Invention

It has been reported that when M-aldehyde or ACR is contained in the carbon dioxide used in the process of precipitating methionine, there occurs some problems in that methionine crystal after precipitation shows polymorphism, and the color of methionine is changed. Further, M-aldehyde and ACR have a strong odor and may cause malodor. Accordingly, it is necessary to remove M-aldehyde and ACR in advance such that the carbon dioxide gas used does not contain M-aldehyde or ACR.

The purification method disclosed in Patent Document 1 is conducted at a high pressure of 6 bar (gauge pressure of 0.6 MPa) ([0050]), and a large production apparatus cost is required to adopt an apparatus that can withstand the pressure. Additionally, it is necessary to treat waste water generated by purification with water, and the treatment cost is also required. Moreover, although Patent Document 1 discloses the removal of MM, there is no description or suggestion as to whether it can be applied to the removal of M-aldehyde or ACR.

In view of the above circumstances, an object of the present invention is to provide a purification method for purifying recovered carbon dioxide gas and a method for producing methionine comprising a purification step of recovered carbon dioxide gas.

Means to Solve Problems

The present inventors have intensively studied, and as a result, found a method for purifying recovered carbon dioxide in which M-aldehyde is removed by using activated carbon from recovered carbon dioxide gas containing M-aldehyde and the like, and thereby purifying recovered carbon dioxide gas under a relatively low pressure, and have completed the present invention.

The present invention encompasses the following embodiments.

The method for purifying carbon dioxide gas as described herein (hereinafter, sometimes referred to as "Method of the present invention") comprises

[1] Contacting carbon dioxide gas containing at least one of 3-methylmercaptopropionaldehyde and acrolein with activated carbon to remove at least one of the 3-methylmercaptopropionaldehyde and acrolein, which includes the following embodiments.

[2] The method for purifying recovered carbon dioxide wherein the carbon dioxide gas is a carbon dioxide gas which is recovered from at least one step of the following steps (1) and (2) comprised in a method for producing methionine: (1) a hydantoin step: 3-methylmercaptopropionaldehyde cyanohydrin is reacted with carbon dioxide and ammonia to obtain 5-(2-methylmercaptoethyl)hydantoin, (2) a hydrolysis reaction step: the 5-(2-methylmercaptoethyl)hydantoin is hydrolyzed in the presence of an alkali compound to obtain the reaction solution containing an alkali salt of methionine.

[3] The method for purifying recovered carbon dioxide according to [1] or [2], wherein the carbon dioxide is recovered carbon dioxide recovered from a process of producing methionine comprising the following steps A to E:

A. a step of reacting methyl mercaptan with acrolein to obtain 3-methylmercaptopropionaldehyde;

B. a step of reacting 3-methylmercaptopropionaldehyde obtained in step A) with hydrocyanic acid (i.e., hydrogen cyanide) to obtain 3-methylmercaptopropionaldehyde cyanohydrin;

C. a step of reacting 3-methylmercaptopropionaldehyde cyanohydrin obtained in step B) with carbon dioxide and ammonia or ammonium carbonate to obtain 5-(2-methylmercaptoethyl)hydantoin;

D. a step of hydrolyzing 5-(2-methylmercaptoethyl)hydantoin obtained in step C) in the presence of an alkali compound to obtain a reaction solution containing an alkali salt of methionine; and E. a step of introducing carbon dioxide into the reaction solution containing the alkali salt of methionine produced in step D) to precipitate methionine, followed by separating the precipitated methionine.

[4] The method for purifying recovered carbon dioxide according to any one of [1] to [3], which is characterized in that before the removal with activated carbon, the carbon dioxide concentration of the recovered carbon dioxide is 70 vol % or more and 99.99 vol % or less.

[5] The method for purifying recovered carbon dioxide according to any one of [1] to [4], which is characterized in that before the removal with activated carbon, the pressure of the recovered carbon dioxide is −0.01 MPa or more and 0.5 MPa or less as gauge pressure (hereinafter, the unit of gauge pressure is sometimes referred to as "MPaG").

[6] The method for purifying recovered carbon dioxide according to any one of [1] to [5], which is characterized in that the activated carbon has an average particle diameter of 0.1 mm or more and 5.0 mm or less, a specific surface area of 1000 $m^2/g$ or more and 1800 $m^2/g$ or less, or a total pore volume of 0.2 mL/g or more and 0.6 mL/g or less.

[7] A method for producing methionine which is characterized by comprising the following steps (1) to (4):

(1) a hydantoin step: a step of reacting 3-methylmercaptopropionaldehyde cyanohydrin with carbon dioxide and ammonia to obtain 5-(2-methylmercaptoethyl) hydantoin;

(2) a hydrolysis reaction step: a step of hydrolyzing the 5-(2-methylmercaptoethyl)hydantoin in the presence of an alkali compound to obtain a reaction solution containing an alkali salt of methionine;

(3) a crystallization step: a step of introducing carbon dioxide into the reaction solution to obtain methionine from the reaction solution; and (4) a step for purifying the recovered carbon dioxide which comprises contacting the recovered carbon dioxide gas containing at least one of 3-methylmercaptopropionaldehyde and acrolein recovered from at least one of the steps (1) and (2) with activated carbon to remove at least one of the contained 3-methylmercaptopropionaldehyde and acrolein (hereinafter, referred to as "Method for producing methionine of the present invention").

[8] The method for producing methionine according to [7] comprising the following steps:

A. a step of reacting methyl mercaptan with acrolein to obtain 3-methyl mercaptopropionaldehyde;

B. a step of reacting the 3-methylmercaptopropionaldehyde with hydrocyanic acid (hydrogen cyanide) to obtain 3-methylmercaptopropionaldehyde cyanohydrin;

C. a step of reacting the 3-methylmercaptopropionaldehyde cyanohydrin with carbon dioxide and ammonia or ammonium carbonate to obtain 5-(2-methylmercaptoethyl)hydantoin;

D. a step of hydrolyzing the 5-(2-methylmercaptoethyl) hydantoin in the presence of an alkali compound to obtain a reaction solution containing an alkali salt of methionine; and, E. a step of introducing carbon dioxide into the reaction solution containing the alkali salt of methionine, precipitating methionine, and separating the precipitated methionine, and A step of contacting the recovered carbon dioxide gas containing at least one of 3-methylmercaptopropionaldehyde and acrolein recovered from at least one of steps C or D with an activated carbon, and purifying the recovered carbon dioxide gas by removing at least one of 3-methylmercaptopropionaldehyde and acrolein.

According to the method of the present invention, it is possible to remove M-aldehyde and the like without increasing the recovered carbon dioxide gas to a high pressure by removing M-aldehyde and the like contained in the recovered carbon dioxide gas with activated carbon. Accordingly, it is not necessary to consider the pressure resistance of the apparatus using the recovered carbon dioxide gas, and the cost of the production apparatus can be suppressed even when the production scale is expanded. Also, compared with the case where M-aldehyde or the like is removed with water, moisture in the carbon dioxide after purification can be kept low.

According to the second and third aspects as described herein, the recovered carbon dioxide gas is carbon dioxide gas recovered from at least one of the hydantoin step and the hydrolysis reaction step, included in the method for producing methionine, and thus the cost of production apparatus for producing methionine can be reduced.

According to the fourth aspect of the present application, the carbon dioxide concentration of the recovered carbon dioxide gas before the removal with activated carbon is 70 volume % or more and 99.99 volume % or less, so that M-aldehyde or the like contained in the recovered carbon dioxide gas can be removed more appropriately, and also the carbon dioxide after the purification can be used as it is in the crystallization step.

According to the fifth aspect of the present application, the pressure of the recovered carbon dioxide before the removal with activated carbon is −0.01 MPa or more and 0.5 MPa or less as gauge pressure, so that the pressure resistance of the apparatus using the recovered carbon dioxide can be lowered, and the cost of production apparatus can be reduced.

According to the sixth aspect of the present application, the activated carbon has an average particle diameter of 0.1 mm or more and 5.0 mm or less, a specific surface area of 1000 $m^2/g$ or more and 1800 $m^2/g$ or less, or a total pore volume of 0.2 mL/g or more and 0.6 mL/g or less, so that an adsorption performance to M-aldehyde or the like can be maintained. Also, the pressure drop in the apparatus using activated carbon can be suppressed, and the pressure of the gas transferred to this process can be lowered.

According to the seventh and eighth aspects of the present application, the method for producing methionine comprises the purification steps of the recovered carbon dioxide gas according to the second to sixth aspects, so that the cost of the methionine production apparatus can be suppressed.

BRIEF DESCRIPTION OF DRAWINGS

FIG. 1 indicates a flowchart of the purification method of the recovered carbon dioxide according to the embodiment as described herein.

FIG. 2 indicates an explanatory drawing of schematic constitution of the purification test apparatus in the purification method using activated carbon.

FIG. 3 indicates an explanatory drawing of schematic constitution of the purification test apparatus in the purification method using water.

MODE FOR CARRYING OUT THE INVENTION

Hereinafter, an embodiment of the method of the present application will be described by indicating examples.

Firstly, a method for producing methionine is explained.

Methionine is produced usually by a production method comprising the following steps.

A. M-aldehyde step: a step of reacting MM with ACR to obtain M-aldehyde;

B. Cyanhydrin step: a step of reacting the M-aldehyde with hydrocyanic acid (hydrogen cyanide) to obtain 3-methylmercaptopropionaldehyde cyanohydrin (hereinafter sometimes referred to as "MCH");

C. Hydantoin step: a step of reacting the MCH with carbon dioxide and ammonia (or ammonium carbonate) to obtain 5-(2-methylmercaptoethyl)hydantoin;

D. Hydrolysis reaction step: a step of hydrolyzing the 5-(2-methylmercaptoethyl)hydantoin in the presence of an alkali compound to obtain a reaction solution containing an alkali salt of methionine; and E. Crystallization step: a step of introducing carbon dioxide into the reaction solution, thereby precipitating methionine, and separating the precipitated methionine to obtain methionine.

Through the above steps A to E, methionine can be obtained industrially. The chemical reaction in each step can be expressed by the following chemical scheme.

A. M-Aldehyde Step

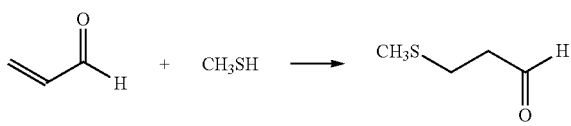

B. Cyanhydrin Step

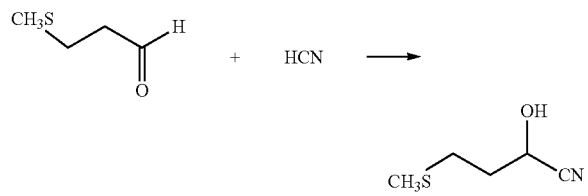

C. Hydantoin Step

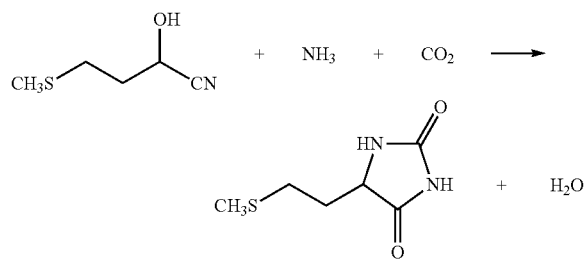

D. Hydrolysis Reaction Step

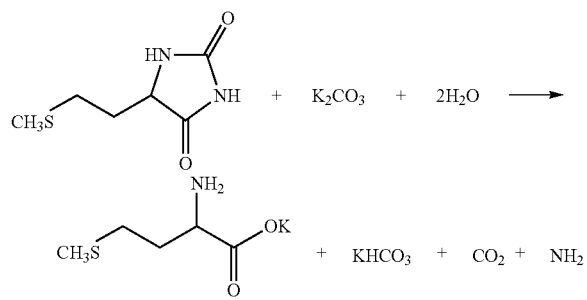

E. Crystallization Step

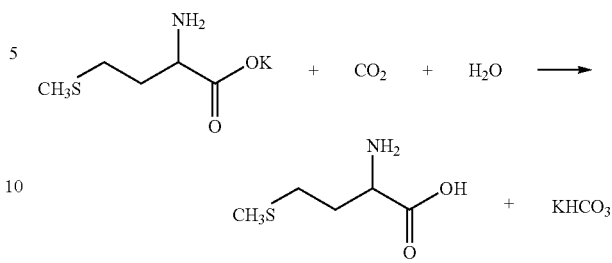

[(1) Hydantoin Step]

The hydantoin step is a step in which MCH forms a hydantoin with carbon dioxide and ammonia to obtain 5-(2-methylmercaptoethyl)hydantoin. The carbon dioxide and ammonia sources used in the hydantoin step may be those usually used, and an excess of the theoretical amount, preferably 1 to 4 moles of carbon dioxide and ammonia per mole of MCH is used. Also, ammonium carbonate or ammonium bicarbonate may be used instead of the combination of carbon dioxide and ammonia. A general condition such as a reaction temperature of about 60 to 85° C. and a residence time of about 3 to 6 hours are used.

FIG. 1 shows a flowchart of a method for purifying recovered carbon dioxide gas according to an embodiment of the present invention. As shown in FIG. 1, in the present embodiment, carbon dioxide is obtained by recovering carbon dioxide that is used in excess amount in the hydantoin step or carbon dioxide that is generated by decomposition of ammonium carbonate. The recovered carbon dioxide contains ACR that is remained unreacted in the M-aldehyde step, which is the previous step of the hydantoin step, and M-aldehyde that is remained unreacted in the cyanohydrin step.

[(2) Hydrolysis Reaction Step]

The hydrolysis reaction step is a step of obtaining a reaction solution by hydrolyzing 5-(2-methylmercaptoethyl)hydantoin in the presence of an alkali compound. Examples of the alkali compound used in this reaction step include potassium hydroxide, sodium hydroxide, potassium carbonate, potassium hydrogen carbonate and the like, and two or more of them can be also used if necessary. The amount of the alkali compound used is usually 2 to 10 mol, preferably 3 to 6 mol as potassium or sodium per mol of 5-(2-methylmercaptoethyl)hydantoin. Also the amount of water used is usually 2 to 20 parts by weight per part by weight of 5-(2-methylmercaptoethyl)hydantoin.

The hydrolysis reaction conducted in the hydrolysis reaction step is a stirring type or a non-stirring type, and is conducted in a continuous type or batch type reactor.

This hydrolysis reaction is preferably carried out by heating to about 150 to 200° C. under pressurized pressure of about 0.5 to 1 MPa as a gauge pressure. The reaction period is usually 10 minutes to 24 hours.

As shown in FIG. 1, in this embodiment, the recovered carbon dioxide gas is obtained by recovering the gas generated in the hydrolysis reaction step. The recovered carbon dioxide gas contains ACR and M-aldehyde.

[(3) Crystallization Step]

In the crystallization step, the reaction solution obtained in the hydrolysis reaction step is allowed to flow into the crystallization apparatus, carbon dioxide is introduced into the reaction solution, and a crystallization is conducted in the reaction solution to obtain methionine precipitates. In this reaction, carbon dioxide is absorbed into the hydrolysis reaction solution by introduction of carbon dioxide, and the alkali salt of methionine is precipitated as free methionine.

[Purification of Recovered Carbon Dioxide]

The recovered carbon dioxide gas obtained in the (1) hydantoin step and (2) hydrolysis reaction step contains ACR and M-aldehyde. These are removed using activated carbon. As shown in FIG. 1, the recovered carbon dioxide gas obtained in (1) the hydantoin step and (2) the hydrolysis reaction step can be also mixed. In this case, it flows into a M-aldehyde removal apparatus through one transport pipe and is purified. The removal apparatus for M-aldehyde, etc. is provided with a packed tower filled with activated carbon. The filling rate of activated carbon is usually 0.3 g/mL or more and 1.0 g/mL or less, preferably 0.35 g/mL or more and 0.6 g/mL or less. The number of the packed towers may be one or two or more, however the following description is an explanation when two packed towers are provided in parallel. Two packed towers provided in parallel (the two packed towers are referred to as "first packed tower" and "second packed tower") are used alternately without interrupting the purification action, thereby M-aldehyde and the like is removed, so that the recovered carbon dioxide is purified. Specifically, the recovered carbon dioxide gas is flowed into the first packed column of the two packed columns to remove M-aldehyde and the like. The conditions for flowing the recovered carbon dioxide gas into the packed tower are preferably that the flow rate is 0.03 m/s or more and 0.2 m/s or less as linear velocity, and the pressure is −0.01 MPa or more and 0.5 MPa or less as gauge pressure. At this time, in the second packed tower, the adsorption ability of the activated carbon is recovered by removing M-aldehyde and the like that is adsorbed on the activated carbon. When the adsorption capacity of the activated carbon is recovered in the second packed tower, the recovered carbon dioxide gas is allowed to flow into the second packed tower, and the adsorption capacity of the activated carbon for the first packed tower is recovered. Accordingly, in the case of two packed towers, they can be also used alternately. Though the case of two packed towers is explained, similarly in the case of three or more packed towers, any packed towers which are not used for removal M-aldehyde and the like in the recovered carbon dioxide is recovered its adsorption capacity during not used in the purification. Accordingly, when a plural of packed columns with activated carbon are set, M-aldehyde and the like in the recovered carbon dioxide gas can be removed continuously by conducting adsorption and desorption in parallel.

In order to recover the adsorption capacity of the activated carbon, an inert gas is circulated in the packed tower. Examples of the inert gas include nitrogen, argon, and helium. The operating pressure and temperature at this time depend on the vapor pressure of the substance to be desorbed from the activated carbon, but preferably from vacuum to atmospheric pressure, and the operating temperature is from 10° C. to the boiling point of the substance to be desorbed at the desorption operating pressure, or more.

In the apparatus for removing M-aldehyde or the like, the concentration of carbon dioxide in the recovered carbon dioxide gas immediately before entering the packed column filled with activated carbon is preferably 70 volume % or more and 99.99 volume % or less. Due to such a component constitution, M-aldehyde and the like in the recovered carbon dioxide gas can be removed more appropriately, and also the carbon dioxide gas can be used as it is after purification in the crystallization step.

Also, in the M-aldehyde removal apparatus, the pressure of the recovered carbon dioxide gas immediately before entering the packed tower filled with activated carbon is preferably −0.01 MPa or more and 0.5 MPa or less as gauge pressure. Since it is not necessary to carry out at a high pressure as disclosed in Patent Document 1, the cost of production apparatus can be suppressed. An adsorption of M-aldehyde or the like on activated carbon is sufficiently achieved by setting the pressure to −0.01 MPa or more, and an introduction of the recovered carbon dioxide gas from the hydantoin step or the hydrolysis reaction step can be easily performed by setting the pressure to 0.5 MPa or less.

The activated carbon material is preferably derived from natural products. For example, wood and coconut shells are preferably raw materials.

The average particle size of the activated carbon is preferably 0.1 mm or more and 5.0 mm or less. By setting in this range, the adsorption performance of M-aldehyde and the like can be maintained. If it is smaller than this range, the pressure drop in the packed tower becomes large, which becomes disadvantageous. The average particle diameter is a 50% particle diameter (D50) described by JIS K1474, and can be measured by the method described in this standard. Also, the specific surface area is preferably 1000 $m^2$/g or more and 1800 $m^2$/g or less. Also the total pore volume is preferably 0.2 mL/g or more and 0.6 mL/g or less.

Carbon dioxide after purification from which M-aldehyde and the like have been removed by the above-mentioned activated carbon can be introduced into the reaction solution in (3) crystallization step, and used for methionine precipitation. Since ACR and M-aldehyde is not contained in carbon dioxide after the purification, it is possible to obtain methionine with high purity.

EXAMPLES

Next, examples of the present invention are shown below, but the present invention is not limited thereto.

Example

FIG. 2 is an explanatory diagram of a schematic constitution of a purification test apparatus 10 for conducting out a purification method using activated carbon. The purification test apparatus 10 is provided with one packed column 11, and supplied with the recovered carbon dioxide obtained in the (1) hydantoin step and (2) hydrolysis reaction step from the left side on the paper surface of FIG. 2. The supplied recovered carbon dioxide passes through the packed tower 11 filled with activated carbon, and then passes through the flow meter 12. The capacity of the packed tower 11 was 44 mL, and the filled amount of activated carbon was 22.3 g. The flow rate of the recovered carbon dioxide to be passed is adjusted by a valve provided at each location of the purification test apparatus 10, and the flow rate is measured by the flow meter 12. The component amount of the recovered carbon dioxide before and after passing through the packed tower 11 is separately measured with a gas component measuring device. Table 1 shows the measured gas flow rate, gas pressure, and the amount of components of the recovered carbon dioxide before passing through activated carbon. Also, the material of activated carbon used was coconut shell, and the average particle size was 3.56 mm, the specific surface area was 1200 $m^2$/g, and the total pore volume was 0.55 mL/g.

TABLE 1

| Gas Flow Rate | Gas Pressure | Component Amount | | | | |
|---|---|---|---|---|---|---|
| | | $CO_2$ | $N_2$ | MM | ACR | M-aldehyde |
| L/min | MPaG | Vol % | Vol % | Vol · ppm | Vol · ppm | Vol · ppm |
| 4.0 | 0.005 | 82 | 18 | 2050 | 115 | 205 |

Also, Table 2 shows the measured result of the concentration of ACR and M-aldehyde at 10 minutes and 120 minutes as an elapsed time after the start of supply (that is, operating time) when the recovered carbon dioxide is supplied continuously to the purification test apparatus 10. The symbol of "N.D." in the table indicates that measurement cannot be performed, that is, the concentration has not been reached the minimum unit that can be measured by the measuring instrument used in this example. From this result, it was possible to purify carbon dioxide containing ACR and M-aldehyde under low pressure by the method for purifying recovered carbon dioxide in the present embodiment.

| Operation Time | | 10 | 120 |
|---|---|---|---|
| ACR | Vol · ppm | N.D. | N.D. |
| M-aldehyde | Vol · ppm | N.D. | N.D. |

Comparative Example

FIG. 3 is an explanatory diagram of a schematic constitution of a purification test apparatus 30 for conducting out a purification method using water instead of activated carbon. The purification test apparatus 30 is provided with one gas-liquid mixing tower 31, and the recovered carbon dioxide obtained in (1) the hydantoin process and (2) the hydrolysis reaction process is supplied from the lower left side on the paper surface of FIG. 3. The supplied recovered carbon dioxide passes through the gas-liquid mixing tower 31 and then passes through the flow meter 32. The flow rate of the recovered carbon dioxide to be passed is measured by the flow meter 32. Also the water that flows into the gas-liquid mixing tower 31 is pure water, and flows into the gas-liquid mixing tower 31 from the upper left side on the paper surface of FIG. 3 via valve 34. The component amount of the recovered carbon dioxide before and after passing through the gas-liquid mixing tower 31 is separately measured by a gas component measuring device. Table 3 shows the measured gas flow rate, gas pressure, and the component amount of the recovered carbon dioxide before passing through the gas-liquid mixing tower 31.

TABLE 3

| Gas Flow Rate | Gas Pressure | Component Amount | | | | |
|---|---|---|---|---|---|---|
| | | $CO_2$ | $N_2$ | MM | ACR | M-aldehyde |
| L/min | MPaG | Vol % | Vol % | Vol · ppm | Vol · ppm | Vol · ppm |
| 4.0 | 0.005 | 82 | 18 | 2200 | 150 | 130 |

Also table 4 shows the results when the recovered carbon dioxide was continuously supplied to the washing test apparatus 30. The ratio of gas-liquid mixing represents the amount of the recovered carbon dioxide supplied per weight of supplied water. From this result, it can be found that when the recovered carbon dioxide of this embodiment is purified with water under low pressure, M-aldehyde can be removed, but ACR is not completely removed, and it can be thus understood that a complete removal is difficult.

| Ratio of gas-liquid (L/G) [wt/wt] | | 5 |
|---|---|---|
| ACR | Vol · ppm | 20 |
| M-aldehyde | Vol · ppm | N.D. |

INDUSTRIAL APPLICABILITY

The purification method of the present invention can be applied regardless of the production of methionine as long as the target to be purified is a recovered carbon dioxide containing any one of M-aldehyde and ACR.

EXPLANATION OF SYMBOL 10, 30 Purification test apparatus
11 Packed tower
12, 32 Flowmeter
31 Gas-liquid mixing tower
34 Valve

The invention claimed is:
1. A method for producing methionine comprising the following steps:
   A. a step of reacting methyl mercaptan with acrolein to obtain 3-methyl mercaptopropionaldehyde;
   B. a step of reacting the 3-methylmercaptopropionaldehyde with hydrocyanic acid (hydrogen cyanide) to obtain 3-methylmercaptopropionaldehyde cyanohydrin;
   C. a step of reacting the 3-methylmercaptopropionaldehyde cyanohydrin with carbon dioxide and ammonia or ammonium carbonate to obtain 5-(2-methylmercaptoethyl)hydantoin;
   D. a step of hydrolyzing the 5-(2-methylmercaptoethyl) hydantoin in the presence of an alkali compound to obtain a reaction solution containing an alkali salt of methionine; and,
   E. a step of introducing carbon dioxide into the reaction solution containing the alkali salt of methionine, precipitating methionine, and separating the precipitated methionine, and
   further comprising at least one of 1) a step of recovering carbon dioxide gas used in an excess amount in the step C and 2) a step of recovering carbon dioxide gas generated in the step D, wherein the recovered carbon dioxide gas contains at least one of acrolein that remains unreacted in the step A and 3-methylmercaptopropionaldehyde that remains unreacted in the step B, and
   further comprising a step of contacting the recovered carbon dioxide gas with an activated carbon, and purifying the recovered carbon dioxide gas by removing at least one of the 3-methylmercaptopropionaldehyde and the acrolein.
2. The method for producing methionine according to claim 1,
   wherein the method comprises both the step of recovering the carbon dioxide gas used in excess amount in the step C and a step of recovering the carbon dioxide gas generated in the step D.

3. The method for producing methionine according to claim 2,
 wherein the recovered carbon dioxide gas used in excess amount in the step C and the recovered carbon dioxide gas generated in the step D are mixed and the mixed recovered carbon dioxide gas is contacted with the activated carbon.

* * * * *